(12) United States Patent
Nam et al.

(10) Patent No.: US 6,441,554 B1
(45) Date of Patent: Aug. 27, 2002

(54) APPARATUS FOR GENERATING LOW TEMPERATURE PLASMA AT ATMOSPHERIC PRESSURE

(75) Inventors: Kee-Seok Nam; Sang-Ro Lee; Jong-Ju Rha; Koo-Hyun Lee; Jong-Kuk Kim, all of Kyungsangnam-do (KR)

(73) Assignee: SE Plasma Inc. (KR)

( * ) Notice: Subject to any disclaimer, the term of this patent is extended or adjusted under 35 U.S.C. 154(b) by 0 days.

(21) Appl. No.: 09/854,655

(22) Filed: May 14, 2001

(30) Foreign Application Priority Data

Nov. 28, 2000 (KR) ......................................... 2000-71178
Feb. 12, 2001 (KR) ........................................... 2001-6653

(51) Int. Cl.[7] ................................................ H01J 7/24
(52) U.S. Cl. ................................ 315/111.21; 118/723 R
(58) Field of Search ....................... 315/111.21, 111.71; 313/309, 351; 118/723 R, 723 E

(56) References Cited

U.S. PATENT DOCUMENTS

| | | | |
|---|---|---|---|
| 5,124,173 A | 6/1992 | Uchiyama et al. | ............. 427/38 |
| 5,275,665 A | 1/1994 | Okazaki et al. | ........... 118/723 E |
| 5,384,167 A | 1/1995 | Nishiwaki et al. | ........... 427/569 |
| 5,414,324 A | 5/1995 | Roth et al. | .............. 315/111.21 |
| 5,549,780 A | * 8/1996 | Koinuma et al. | ........ 118/723 E |

OTHER PUBLICATIONS

S. Kanazawa et al., *Stable Glow Plasma At Atmospheric Pressure*, Journal Of Physics, Applied Physics, vol. 21, pp. 838–840 (Feb. 23, 1988).

T. Yokoyama et al., *The Mechanism Of The Stabilisation Of Glow Plasma At Atmospheric Pressure*, Journal of Physics, Applied Physics, vol. 23, pp. 1125–1128 (May 8, 1990).

A. Schütze et al., *The Atmospheric–Pressure Plasma Jet: A Review and Comparison To Other Plasma Sources*, IEEE Transactions On Plasma Science, vol. 26, No. 6, pp. 1685–1694 (Dec. 1998).

B. Eliasson, *Nonequilibrium Volume Plasma Chemical Processing*, IEEE Transactions Of Plasma Science, vol. 19, No. 6, pp. 1063–1077 (Dec. 1991).

U. Kogelschatz, *From Ozone Generators To Flat Television Screens: History And Future Potential Of Dielectric–barrier Discharges*, Pure Applied Chemistry, vol. 71, No. 10, pp. 1819–1828 (Aug. 1999).

* cited by examiner

Primary Examiner—Don Wong
Assistant Examiner—Thuy Vinh Tran
(74) Attorney, Agent, or Firm—Cooper & Dunham LLP

(57) ABSTRACT

Disclosed is an apparatus for generating low-temp plasma at atmospheric pressure, comprising: a couple of electrodes facing each other at a distance, one of them being connected to a power supply, the other being grounded; a couple of dielectrics with a thickness of 25 $\mu$m–10 mm, positioned on the facing surfaces of the electrodes in such a way as to face each other, one of them having at least one discharge gap therein; and a conductor electrode having at least one tip positioned within the discharge gap, in which an electric field is applied at an intensity of 1–100 KV/cm through the power supply across the electrodes by use of a pulse direct current or an alternating current in a frequency bandwidth of 50 Hz–10 GHz while a reaction gas is fed between the electrodes, so as to induce a hollow cathode discharge, a capillary discharge or the high accumulation of charges from the discharge gap.

4 Claims, 3 Drawing Sheets

APPARATUS FOR GENERATING LOW TEMPERATURE PLASMA AT ATMOSPHERIC PRESSURE

BACKGROUND OF THE INVENTION

1. Field of the invention

The present invention relates to an apparatus for generating low-temperature plasma in a high density at atmospheric pressure with low discharge initiation and maintenance voltages.

2. Description of the Prior Art

Generally, plasma is defined as a partially ionized gas composed of a nearly equal number of positive and negative free charges so that it is electrically neutral. Subgrouped into high-temperature and low-temperature plasma according to the temperature at which it undergoes ionization, plasma is of very high reactivity, chemically and physically.

Low-temperature plasma is used to synthesize various materials, such as metals, semiconductors, polymers, nylon, plastic, paper, fiber, and ozone, or to modify surface properties of materials with a concomitant improvement in various physical and chemical properties such as junction strength, dyeing properties, printability, etc. Accordingly, low-temperature plasma finds numerous applications in semiconductor, metal, ceramic thin film synthesis, and cleaning fields.

Typically, low-temperature plasma can be generated in a vacuum vessel of low pressure. In order to maintain such a vacuum, there is needed an apparatus, which is expensive on the whole. Additionally, if materials to be treated are large in size, it is difficult to apply plasma to them. Another problem with plasma treatment is difficulty in automation of plasma processes. Further to these, plasma has difficulty in treating materials which show high vapor pressures or are degassed, such as rubber, biomaterials, etc.

To avoid these problems, there have been developed various techniques, exemplified by corona discharge, dielectric barrier discharge and glow discharge, by which low-temperature plasma can be generated at atmospheric pressure. These techniques are now applied to a broad range of fields, including synthesis of chemicals, such as ozone, sterilization, detoxification, and synthesis of materials which are difficult to treat with plasma in vacuo, in addition to the fields mentioned above.

A corona discharge is a discharge of electricity appearing as a bluish-purple glow on the surface of and adjacent to a conductor when the voltage gradient exceeds a critical value. In general, by applying a high voltage across two pointed electrodes made of conductive materials, such as metal, streamer plasma is generated from the electrodes. When a voltage is applied across two electrodes with a very short distance therebetween, an arc is generated, forming linear plasma with a very small diameter. At this time, to prevent the plasma from being converted to arc discharge, the voltage is intermittently applied or a resistance is provided to the electrodes.

A dielectric barrier discharge utilizes the charge accumulation resulting from dielectric polarization to form a reverse potential at which the discharge is halted, that is, it takes advantage of a pulse discharge, thereby preventing the development of arc discharges.

In the case of a corona discharge, plasma is generated in the form of a streamer that is not homogeneous and is low in density. Additionally, because the gap between two electrodes is narrow, a corona discharge is difficult to apply to targets of three-dimensional shape. Also, other problems with the coronal discharge include noise generation and a short electrode lifetime.

Although providing homogenous plasma, the dielectric barrier discharge does not ensure the generation of homogenous, diffused plasma over a large area, as in the corona discharge. Where an additional means is provided for preventing the development to an arc discharge, the dielectric barrier discharge is low in plasma density, and the distance between two electrodes is so narrow as to limit the size and shape of a target to be treated.

When gases with high discharge initiation and maintenance potentials, such as argon, oxygen and nitrogen, are used, both the corona discharge and the dielectric barrier discharge techniques require a high-voltage power supply. However, the power supply is difficult to operate and manage because of its being expensive and high in electricity consumption.

SUMMARY OF THE INVENTION

Therefore, it is an object of the present invention to overcome the above problems encountered in prior arts and to provide an apparatus for generating low-temperature plasma at atmospheric pressure, which has such a novel structure of electrodes as to prevent the conversion of the plasma to an arc discharge.

It is another object of the present invention to provide a plasma-generating apparatus, which is so low in discharge voltage as to greatly reduce the operating and installment cost and electricity consumption of the power supply equipped.

It is a further object of the present invention to provide a plasma-generating apparatus, which can take advantage of alternating currents and pulse direct currents in a broad bandwidth of frequencies.

It is still a further object of the present invention to provide a plasma-generating apparatus, which can discharge in gases of high discharge initiation potentials, such as nitrogen, oxygen and the air.

It is still another object of the present invention to provide a plasma-generating apparatus, which can generate a homogeneous, high-density, low-temperature plasma at a low discharge voltage over a large area.

Based on the present invention, the above objects could be accomplished by a provision of an apparatus for generating low-temperature plasma at atmospheric pressure, comprising: a couple of electrodes facing each other at a distance, one of them being connected to a power supply, the other being grounded; a couple of dielectrics with a thickness of 25 $\mu$m–10 mm, positioned on the facing surfaces of the electrodes in such a way as to face each other, one of them having at least one discharge gap therein; and a conductor electrode having at least one tip positioned within the discharge gap, in which an electric field is applied at an intensity of 1–100 KV/cm through the power supply across the electrodes by use of a pulse direct current or an alternating current in a frequency bandwidth of 50 Hz–10 GHz while a reaction gas is fed between the electrodes.

The plasma generated from the apparatus of the present invention is suitable to form radicals of high energy, which have numerous applications in various fields, including bonding, polishing, cleaning, thin films deposition, sterilization, disinfection, ozone generation, printing, dyeing, etching of various materials such as metal, rubber, fibers, paper, synthetic resins and semiconductors. Also, application fields of the plasma include purification of tap water and waste water, purification of air and automobile exhaust gas such as $SO_x$ and $NO_X$, combustion of fuels, manufacture of highly luminous lamps, etc.

BRIEF DESCRIPTION OF THE INVENTION

The above and other objects, features and other advantages of the present invention will be more clearly understood from the following detailed description taken in conjunction with the accompanying drawings, in which.

DETAILED DESCRIPTION OF THE PREFERRED EMBODIMENTS

Figure 1:
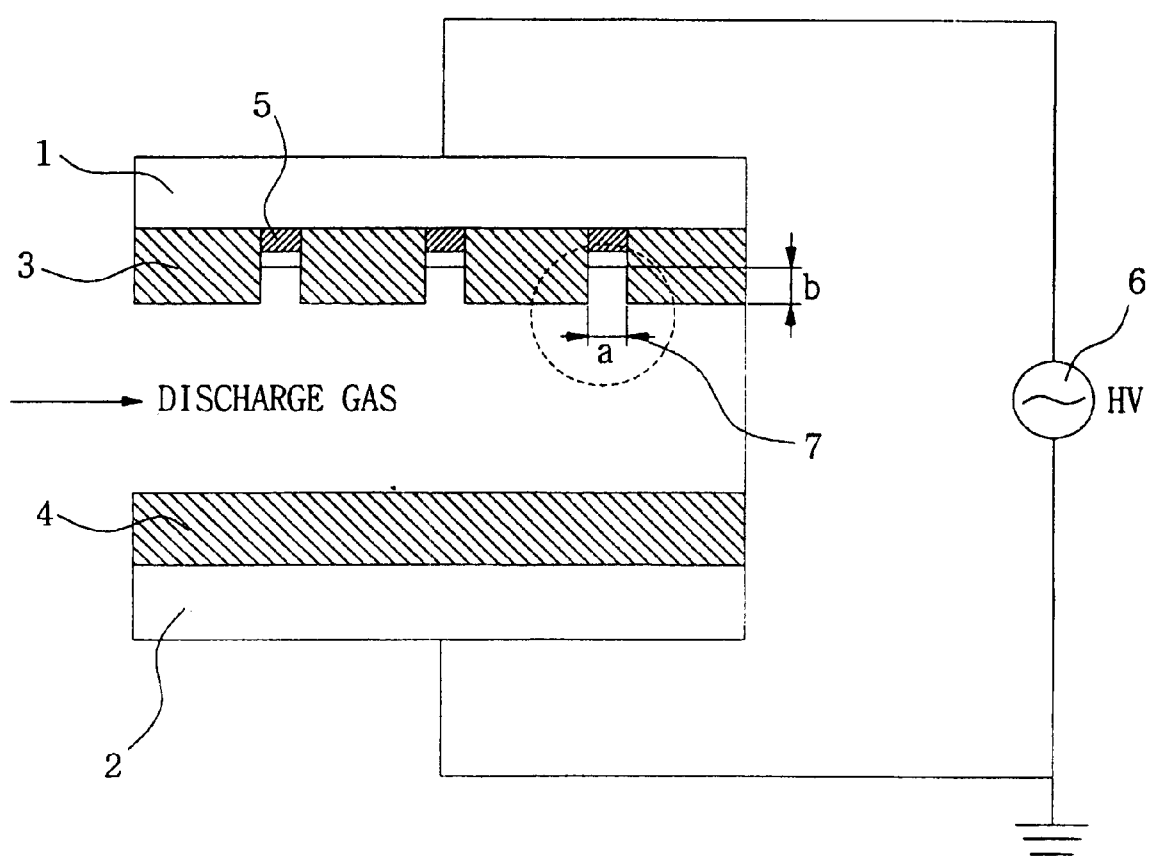
FIG. 1 is a schematic diagram showing a plate structure of electrodes in a cross sectional view, suitable for use in an apparatus for generating low-temperature plasma at atmospheric pressure, in accordance with a first embodiment of the present invention.

The application of the preferred embodiments of the present invention is best understood with reference to the accompanying drawings, wherein like reference numerals are used for like and corresponding parts, respectively.

[First Embodiment]

With reference to FIG. 1, there is an electrode structure seen in a cross sectional view, suitable for use in an apparatus for generating low-temperature plasma at atmospheric pressure, in accordance with a first embodiment of the present invention. In this embodiment, the present invention employs a plate structure of electrodes in generating low-temperature plasma at atmospheric pressure.

As show n in FIG. 1, the apparatus has a couple of electrodes 1 and 2 which are positioned to face each other in accordance with the present invention. One of the two electrodes is connected to a power supply 6 while the other electrode is grounded. When the power supply 6 provides a direct current, the grounded electrode is an anode 2 and the electrode connected to the power supply 6 is set as a cathode 1. Preferably, both electrodes are made of metal such as stainless steel, aluminum or copper.

One of dielectrics 3 and 4 is mounted on each of the electrodes 1 and 2, respectively, and arranged in such a way as to face each other. In order to facilitate the generation of plasma, each of the dielectrics 3 and 4 preferably ranges in thickness from 25 μm to 10 mm. In the dielectric 3 which is mounted onto the power supply-connected electrode 1, discharge gaps 7 are provided which run through the dielectric 3 perpendicularly to its surface. On the other hand, the dielectric 4 mounted onto the surface of the grounded electrode 2 has no discharge gaps. That is, one dielectric with perpendicularly perforating discharge gaps is mounted on the electrode 1 connected to the power supply 6 and another dielectric with no discharge gaps is mounted on the grounded electrode 2, after which the two dielectrics are positioned in such a way as to face each other.

Extended from the electrode 1, conductor electrodes 5 with a certain width (a) and a certain height (b) are positioned within each discharge gap 7. The conductor electrodes 5 have tips 8, 8' or 8" which may be in a form shown in FIG. 3A, 3B or 3C. Upon the application of an electric fields from the power supply 6, the conductor electrodes 5 accumulate charges at the tips 8, 8' or 8" which facilitate the discharging of the accumulated charges. In addition, the tips 8, 8' or 8" function to control the width (a) and height (b) of each of the discharge gaps 7.

Figure 3A:
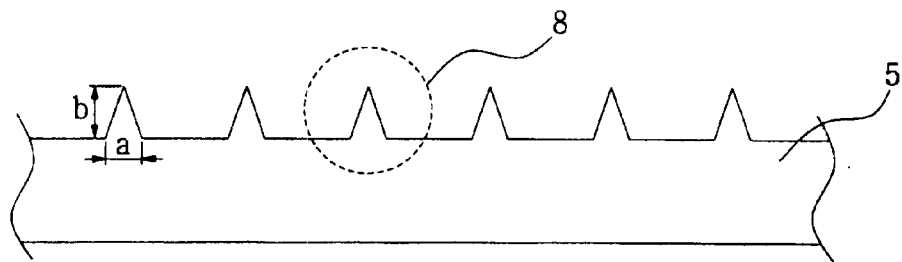
FIG. 3 provides illustrations of tips provided to conductor electrodes.
Figure 3B:
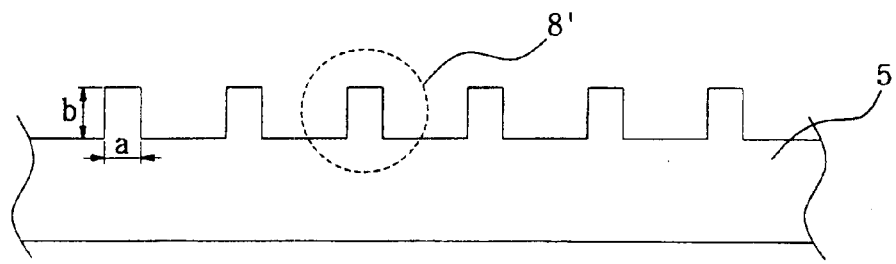
Figure 3C:
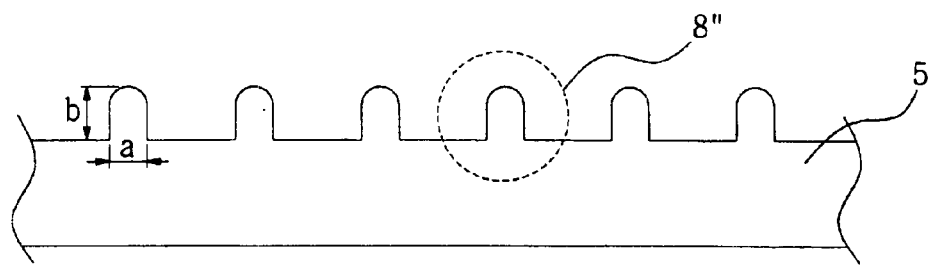

As shown in FIGS. 3A, 3B and 3C, the tips formed on the conductor electrode 5 may be pointed, square or curved ∩ in shape. Other various shapes may be applied to the tips. Preferably, the tips have a height (b) 0.1–20 times as long as their width (a) while being present at a density of 1–100 per length of 10 mm.

Limitations in the size and number of the tips are attributed to the fact that, when the size and number are out of the ranges, the accumulation of charges at the tips is too inefficient to lower the discharge initiation and maintenance voltages, to obtain high-density plasma, and to generate homogeneous plasma.

Although the apparatus having a plate structure of electrodes is illustrated to have the dielectric 3 on the electrode 1 connected to the power supply 6 and the dielectric 4 on the electrode grounded, it should be understood that the present invention is not limited to this, but may have various structures. For example, the electrodes 1 and 2 on which the dielectrics 3 and 4 are to be positioned may be changed in position. That is, the dielectric 3 with discharge gaps 7 is mounted onto the ground electrode 2 while the dielectric 4 lacking discharge gaps 7 is mounted onto the electrode 1 connected to the power supply 6. Additionally, when a dielectric with discharge gaps 7 may be mounted on one of the electrodes 1 and 2, the remaining one may be provided with no dielectrics.

Ranging in thickness from 25 μm to 10 mm, the dielectrics are required to be resistant to high temperatures and have superior dielectric properties. Preferably, the dielectrics are made of a materials selected from the group consisting of glass, alumina, boron nitride, silicon carbide, silicon nitride, quartz, and magnesium oxide.

When no discharge gaps 7 are provided for the dielectric 3, the generation of plasma demands high voltages. The plasma generated is, however, low in density. In contrast, when the dielectric 3 is provided with a conductor electrode 5 having discharge gaps 7 and tips 8, the electric fields applied to the electrodes 1, 2 and 5 are accumulated at the tips and thus intensified thereat, thereby bringing about the effects of a hollow cathode discharge and a capillary discharge in the discharge gaps 7. Accordingly, the voltage needed to generate plasma can be lowered and the plasma generated is high in density and stable.

The discharge gaps 7 which run perpendicularly through the dielectric preferably range in width (a) from 5 μm to 2 mm with a height (a) being 5–250 fold longer than the width (b). If the width and height are out of the limit ranges, no capillary and hollow cathode discharges are generated so that discharge initiation and maintenance potentials cannot be reduced to desired values. In addition, stable high-density plasma cannot be generated, nor can plasma be prevented from being converted to an arc.

[Second Embodiment]

Figure 2:
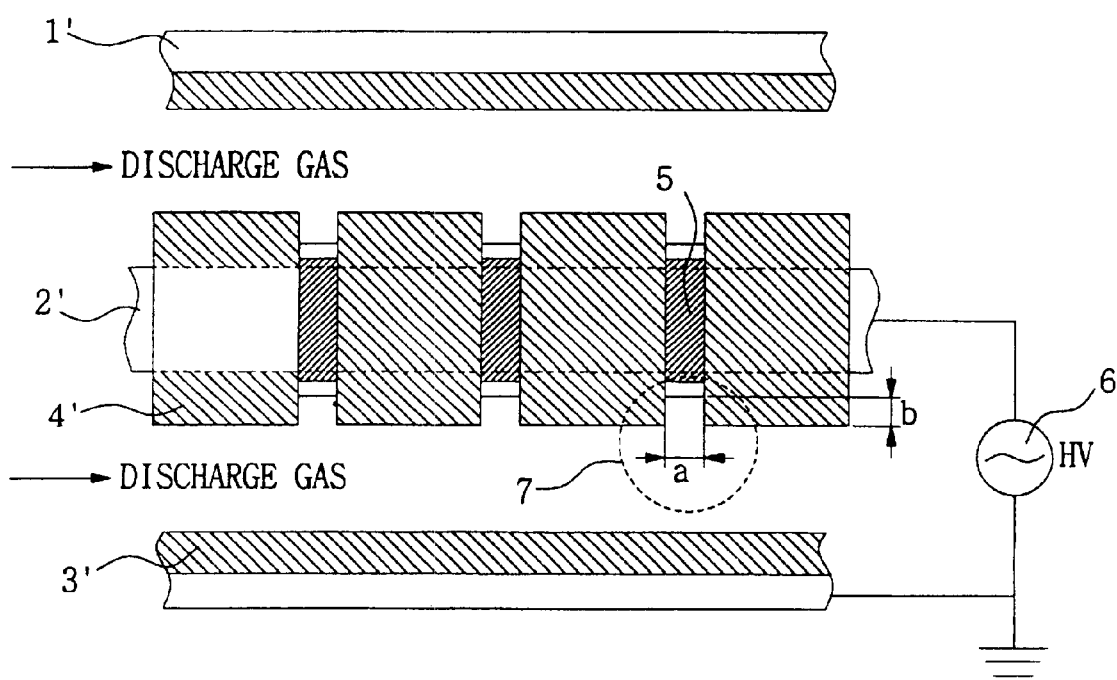
FIG. 2 is a schematic diagram showing a tube structure of electrodes in a cross sectional view, suitable for use in an apparatus for generating low-temperature plasma at atmospheric pressure in accordance with a second embodiment of the present invention.

With reference to FIG. 2, there is an electrode structure seen in a cross sectional view, suitable for use in an apparatus for generating low-temperature plasma at atmospheric pressure, in accordance with another embodiment of the present invention. In this embodiment, the present invention adopts a tube structure of electrodes to an apparatus capable of low-temperature plasma generation at atmospheric pressure.

As seen in FIG. 2, there is provided a tubular electrode 1' to the inner circumference of which a dielectric 3' is attached. Along the central axis of the tubular electrode 1', a cylindrical core electrode 2' which is concentric to the tubular electrode 1' is placed at a certain distance from the dielectric 3' attached to the inner surface of the tubular electrode 1'. Both ends of each electrode are fixed while being suitably insulated (not shown). To the outer circumference of the core electrode 2', another dielectric 4' is fixed, with a plurality of discharge gaps 7' being provided at regular intervals in the dielectric 4'.

The thickness of each of the electrodes 3' and 4' may fall within the range set in the First Embodiment. Also, the same limitations as in the First Embodiment are placed on the width (a) and height (b) of the discharge gaps 7. On the outer circumference of the core electrode 2 are positioned conductor electrodes 5 with such a width (a) and a height (b) as to fit the discharge gaps 7. The conductor electrodes 5 are also provided with tips which have the shapes shown in FIG. 3.

While the tubular electrode 1' is grounded, the core electrode 2' is connected to a power supply 6.

In the tube structure, however, various modifications can be made in arrangements, shapes and conformations of electrodes 1' and 2' and dielectrics 3' and 4'.

In order to generate plasma, an electric field is applied at an intensity of 1–100 KV/cm through the power supply 6 to the apparatuses of the First and the Second Embodiments, by use of a pulse direct current or an alternating current in a frequency bandwidth of 50 Hz–10 GHz. In the presence of such an electric field, discharging is conducted between the tips of the discharge gaps and the counter electrode, to generate plasma.

Using the apparatuses of the present invention, homogeneous plasma of a large area can be generated stably.

The plasma generated from the apparatuses of the present invention is applied to a variety of materials, such as metal, rubber, fibers, paper, and synthetic resins, e.g. plastics, nylon, epoxy, etc., to change surface properties of the materials to ones suitable for use in bonding, polishing, thin films deposition, dyeing, printing, etc.

Also, plasma can be directly applied for the removal of toxicity and the purification of contaminated air. In addition, plasma is used to make ozone which is utilized in sterilization and disinfection of tap water, purification of waste water, purification of automobile exhaust gases such as $SO_x$ and $NO_x$, and complete combustion of fuels in automobile engines. Further to these, plasma can be adopted to manufacture very bright lamps useful for photochemical reactions which can be applied to various surface treatment processes, including semiconductor device fabrication.

For instance, reaction gases, such as air, water vapor, oxygen, nitrogen, hydrogen, argon, helium, methane, ammonia, tetrafluoro carbon, aectylene, propane, etc, are fed, alone or in combination, between the electrodes to which the dielectrics are attached, after which a high electric field is applied through the power supply to generate plasma. This plasma is usefully utilized in bonding, polishing, cleaning, thin films deposition, sterilization, disinfection, ozone preparation, dyeing, printing, etching, purification of water, purification of air and automobile exhaust gases, complete combustion of fuels in automobile engines, manufacture of highly luminous lamps, etc.

EXPERIMENTAL EXAMPLE

This experimental example employed the same plasma-generating apparatus as in Second Embodiment, which had a plate structure in which two electrode plates 1 and 2 were arranged to face each other and a dielectric is provided on each of the facing surfaces of the electrode plates 1 and 2. In one of the dielectrics 3 and 4, a plurality of discharge gaps 7, each being 200 $\mu$m width and 2 mm high, were formed. For the conductor electrodes 5, tips 8 shaped as in FIG. 3a, each having a width (a) of 2 mm and a height (b) of 1.5 mm, were provided. Between the two electrodes 1 and 5, which were 7 mm distant from each other, helium gas was introduced, while a direct current bipolar pulse electric source of 50 KHz was applied across the electrodes to discharge at atmospheric pressure.

As a result, about 1 KV was used to initiate the discharge with a maintenance voltage of about 0.7 KV. Under these conditions, plasma with a high density was stably generated without generating arcs.

At atmospheric pressure, a discharge initiation voltage for helium gas was measured to be about 3.7 KV/cm. If the distance between the electrodes was 7 mm, about 2.6 KV was required as a discharge initiation potential.

As described hereinbefore, the apparatuses for generating low-temperature plasma of the present invention enjoy the following advantages:

First, the apparatus for generating plasma at atmospheric pressure, adapted for the induction of hollow cathode discharges, capillary discharges or highly accumulated electric fields, prevents the conversion of the plasma to arcs and thus gives stable, low-temperature plasma in a high density.

Next, the apparatus can initiate and maintain discharging at very low voltages, and utilizes a broad bandwidth of frequencies, in addition to being low in electricity consumption and being manufactured at a low cost.

Finally, the apparatus can generate homogeneous plasma over a large area in a high density. The plasma is suitable to form radicals of high energy, which have numerous applications in various fields, including bonding, polishing, cleaning, thin films deposition, sterilization, disinfection, ozone preparation, printing, dyeing, etching, purification of tap water and waste water, purification of air and automobile exhaust gas, complete combustion of fuels, manufacture of highly luminous lamps, etc. In these cases, the plasma can bring about excellent results and reduce the treatment time greatly.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. An apparatus for generating low-temperature plasma at atmospheric pressure, comprising:

a couple of electrodes facing each other at a distance, one of them being connected to a power supply, the other being grounded;

a couple of dielectrics with a thickness of 25 $\mu$m–10 mm, positioned on the facing surfaces of the electrodes in such a way as to face each other, one of them having at least one discharge gap therein; and a conductor electrode having at least one tip positioned within the discharge gap, wherein an electric field is applied at an intensity of 1–100 KV/cm through the power supply across the electrodes by use of a pulse direct current or an alternating current in a frequency bandwidth of 50 Hz–10 GHz while a reaction gas is fed between the electrodes.

2. The apparatus as set forth in claim 1, wherein the discharge gap ranges in width from 5 μm to 2 mm with a height being 5–250 times as long as the width.

3. The apparatus as set forth in claim 1, wherein the electrodes are made of metal, and the tip has a height 0.1–20 times as long as its width and is present at a density of 1–100 per 10 mm of the electrode.

4. The apparatus as set forth in claim 1, wherein the dielectrics are made of an insulating material selected from the group glass, alumina, boron nitride, silicon carbide, silicon nitride, quartz, and magnesium oxide.

* * * * *